(12) United States Patent
Szymusiak et al.

(10) Patent No.: US 10,337,959 B2
(45) Date of Patent: Jul. 2, 2019

(54) SYSTEM, METHOD AND APPARATUS FOR MAKING EVIDENT DIESEL EXHAUST FLUID CONTAMINATION

(71) Applicant: Ford Global Technologies, LLC, Dearborn, MI (US)

(72) Inventors: Scott J. Szymusiak, Canton, MI (US); Donald M. Lawrence, Birmingham, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 82 days.

(21) Appl. No.: 15/254,908

(22) Filed: Sep. 1, 2016

(65) Prior Publication Data

US 2018/0058984 A1    Mar. 1, 2018

(51) Int. Cl.
*G01M 15/10* (2006.01)
*G01N 21/78* (2006.01)
*G01N 33/28* (2006.01)

(52) U.S. Cl.
CPC .......... *G01M 15/102* (2013.01); *G01N 21/78* (2013.01); *G01N 33/2835* (2013.01)

(58) Field of Classification Search
CPC ........ F01N 3/021; F01N 13/087; F01N 13/04; F01N 11/00; F01N 3/023; F01N 13/0093; F01N 13/0097; F01N 11/002; F01N 3/031; F01N 2410/14; F01N 2560/06; F01N 2900/1406; F01N 2410/02; F01N 2550/12; F01N 2900/1404; F01N 3/206; F01N 2900/1818; F01N 2900/0421; F01N 2610/02; F01N 3/2066; Y10T 137/1624; Y02T 10/47; Y02T 10/24; G01M 15/102; G01N 33/2835; G01N 21/78; G01N 25/18; G01N 17/006; G01N 33/28; G01N 11/00; G01N 17/002; G01N 17/046; G01N 33/2829; B01D 53/9431; B01D 53/9495

See application file for complete search history.

(56) References Cited

U.S. PATENT DOCUMENTS

| | | | | |
|---|---|---|---|---|
| 4,784,959 | A * | 11/1988 | Wegrzyn | G01M 3/20 252/960 |
| 5,251,564 | A * | 10/1993 | Rim | F01N 3/02 110/216 |
| 5,585,550 | A * | 12/1996 | Frank | G01N 33/2847 141/94 |
| 2004/0011026 | A1 * | 1/2004 | Nakatani | F01N 3/0233 60/286 |
| 2006/0156919 | A1 * | 7/2006 | Sellers | F01N 3/023 95/8 |
| 2008/0245768 | A1 * | 10/2008 | Cottrell | C09D 11/34 216/42 |
| 2013/0115137 | A1 | 5/2013 | Tao et al. | |

(Continued)

*Primary Examiner* — Lore R Jarrett
(74) *Attorney, Agent, or Firm* — Julia Voutyras; McCoy Russell LLP

(57) ABSTRACT

A system, method and apparatus for making evident, diesel exhaust fuel (DEF) contamination is provided. The system, for use with a diesel exhaust fluid system, includes a container having an opening to receive a diesel exhaust fluid. A reactive device is located near the opening and reactive upon exposure to one or more predetermined components potentially present in a fluid pourable into the container through the opening. The reactive device is not reactive to the diesel exhaust fluid.

20 Claims, 3 Drawing Sheets

(56) References Cited

U.S. PATENT DOCUMENTS

2014/0060699 A1* 3/2014 Szymusiak .......... B60K 15/035
  141/285
2014/0196521 A1* 7/2014 Basu ...................... G01N 25/18
  73/25.01

* cited by examiner

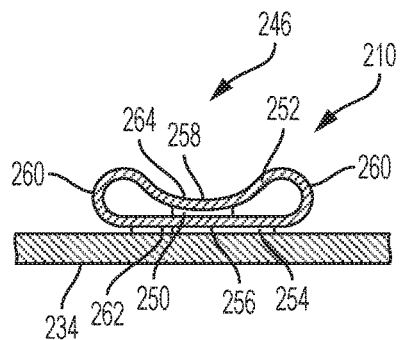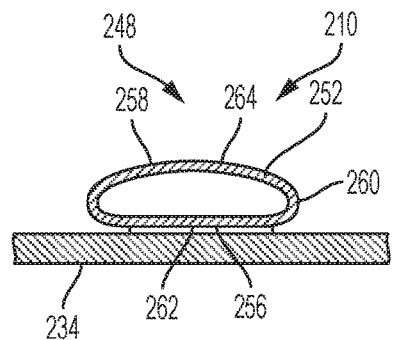
FIG. 4A  FIG. 4B
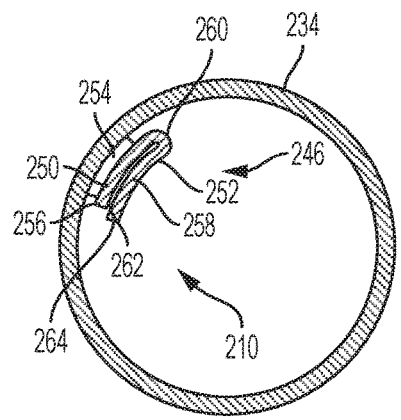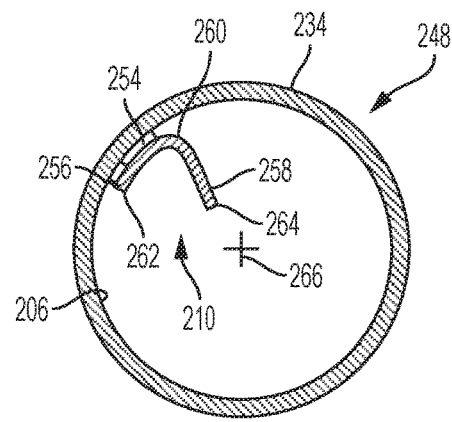
FIG. 5A  FIG. 5B
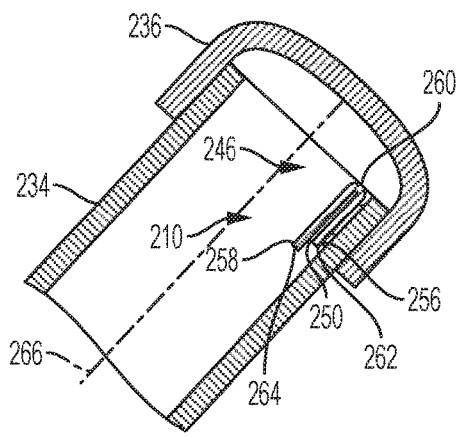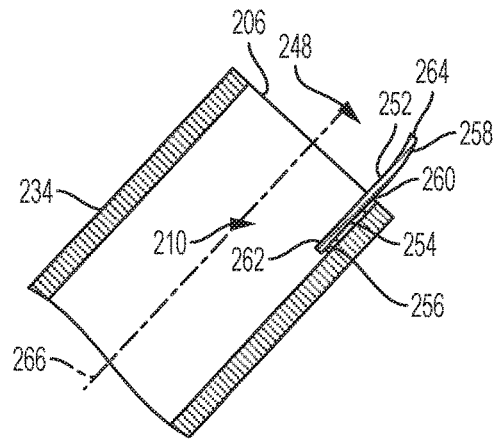
FIG. 6A  FIG. 6B

SYSTEM, METHOD AND APPARATUS FOR MAKING EVIDENT DIESEL EXHAUST FLUID CONTAMINATION

FIELD

The present disclosure relates to the selective catalytic system (SCR) for use with a diesel engine and, in particular, systems, methods, and mechanisms to make contamination of a diesel exhaust fuel evident.

BACKGROUND AND SUMMARY

Efforts to reduce harmful emissions from diesel engines may include reducing CO emissions, unburned hydrocarbons, particulate emissions, and NOx emissions. Measures to reduce one class of emissions may make efforts to reduce others more challenging. For example, running a diesel engine with a lean burn air-to-fuel ratio may increase soot combustion and reduce the level of unburned fuel in the exhaust. However, the excess air in the lean mixture may tend to increase the amount of NOx produced. Conversely, effective techniques to reduce NOx may allow for more aggressive soot combustion. This interdependence, may further increase the importance of NOx reduction measures.

Measures to reduce NOx, may include selective catalytic reduction (SCR). SCR systems may spray, or inject a Diesel Exhaust Fluid (DEF) in regulated doses into the exhaust stream upstream from an SCR catalyst. DEF is typically a 32.5% solution of urea in demineralized water. DEF products may be known commercially as DEF, AdBlue, urea, ARLA, or ARNOX. Once sprayed, or injected, into the exhaust stream the urea may decompose into ammonia and carbon dioxide. Then, within the SCR catalyst, the NOx may be chemically reduced by the ammonia ($NH_3$) into water ($H_2O$) and nitrogen ($N_2$), and released through the exhaust.

The DEF may be stored in a container located onboard diesel powered vehicles. The container may be located in the engine compartment. Engine compartments typically also include storage systems for other liquids for engine and vehicle operation, for example, hydrocarbon materials such as fuels, oils, other lubricants, additives, etc. Because of their relative proximity cross contamination is possible. Avoiding contamination of the reductant fluid, i.e. the DEF, is important for a number of reasons. For example, if contaminated: the effectiveness of reducing NOx with the DEF may be reduced; the remaining DEF may be consumed more quickly than it would otherwise be consumed; the contaminated DEF may cause the SCR system to malfunction, and may damage the engine's exhaust management equipment; and a malfunctioning SCR system may cause the engine to shut down, or cause a vehicle equipped with the system to operate at very slow speeds. In addition, the presence of the contamination in the DEF storage tank may void the equipment manufactures warranty. Once the hydrocarbons are in the reductant system the system may have to be, replaced or, taken apart, cleaned, and rebuilt with some new, and typically expensive, components to replace those that may be destroyed.

Ancillary diesel support systems, such as refueling stations, refueling vehicles, retailers, and various maintenance facilities may include reductant storage, and distribution, systems. These too, may be vulnerable to contamination. Typically these storage systems and other parts of reductant dosing systems are made with materials which may degrade in the presence of hydrocarbons.

Owners and users are warned not to put any products not identified as approved reductants into the DEF system. Warranty agreements may include a warning or clause that the warranty will not cover such misuse/abuse from contaminant introduction. Determining who is responsible for contamination of the DEF, and perhaps for the cost of remediation/repair, and avoiding possible, or further, damage would be advantageous. Also advantageous would be providing early notification of the contamination which may avoid damage, or extensive remediation efforts.

Methods exist to test for hydrocarbons in the reductant fluid. For example, US Patent publication 20130115137 A1 discloses sensing materials for selective and sensitive detection of hydrocarbons suggested implementation via a wearable detector. As another example the firm Bellingham and Stanley make such a product in the form of a test strip that is effective in giving such proof of contamination.

The inventors of the present disclosure have recognized a number of shortcomings of these approaches. For example, the wearable detector disclosed 20130115137 A1 is too far removed from the location of the possible contamination. The problem with the test strips is that the strip must be put into the fluid of the tank or a sample of the fluid must be brought out of the tank in order to test the fluid. Often reductant storage tanks have a long fill pipe, especially those on vehicles. This makes such testing difficult or impossible and so the suspected system must be removed and opened in order to complete the test. This removal and opening of the system is difficult and expensive in itself.

What is needed is an indicator, a system and a method that makes contamination easy to determine and that can be accomplished in close proximity to the DEF storage tank. Embodiments in accordance with the present disclosure provide a system, method and apparatus for making evident, diesel exhaust fluid (DEF) contamination is provided. The system, for use with a diesel exhaust fluid system, may include a container having an opening to receive a diesel exhaust fluid. A reactive device may be located near the opening and reactive upon exposure to one or more predetermined components potentially present in a fluid pourable into the container through the opening. The reactive device may not be reactive to the diesel exhaust fluid.

In this way, contamination, or lack of contamination, may be determined substantially immediately and at the site of the DEF storage tank. Also in this way, a servicing organization that suspects hydrocarbon contamination could confirm the contamination before they work on the system.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or is that follow the detailed description. Furthermore, the claimed subject matter is not limited to implementations that solve any disadvantages noted above or in any part of this disclosure.

BRIEF DESCRIPTION OF THE DRAWINGS

FIGS. 4A-4B are sectional views illustrating an example indicator in respective first and second states in accordance with the present disclosure.

FIGS. 5A-5B are sectional views illustrating another example indicator in respective first and second states in accordance with the present disclosure.

FIGS. 6A-6B are sectional views illustrating another example indicator in respective first and second states in accordance with the present disclosure.

DETAILED DESCRIPTION

Figure 1:
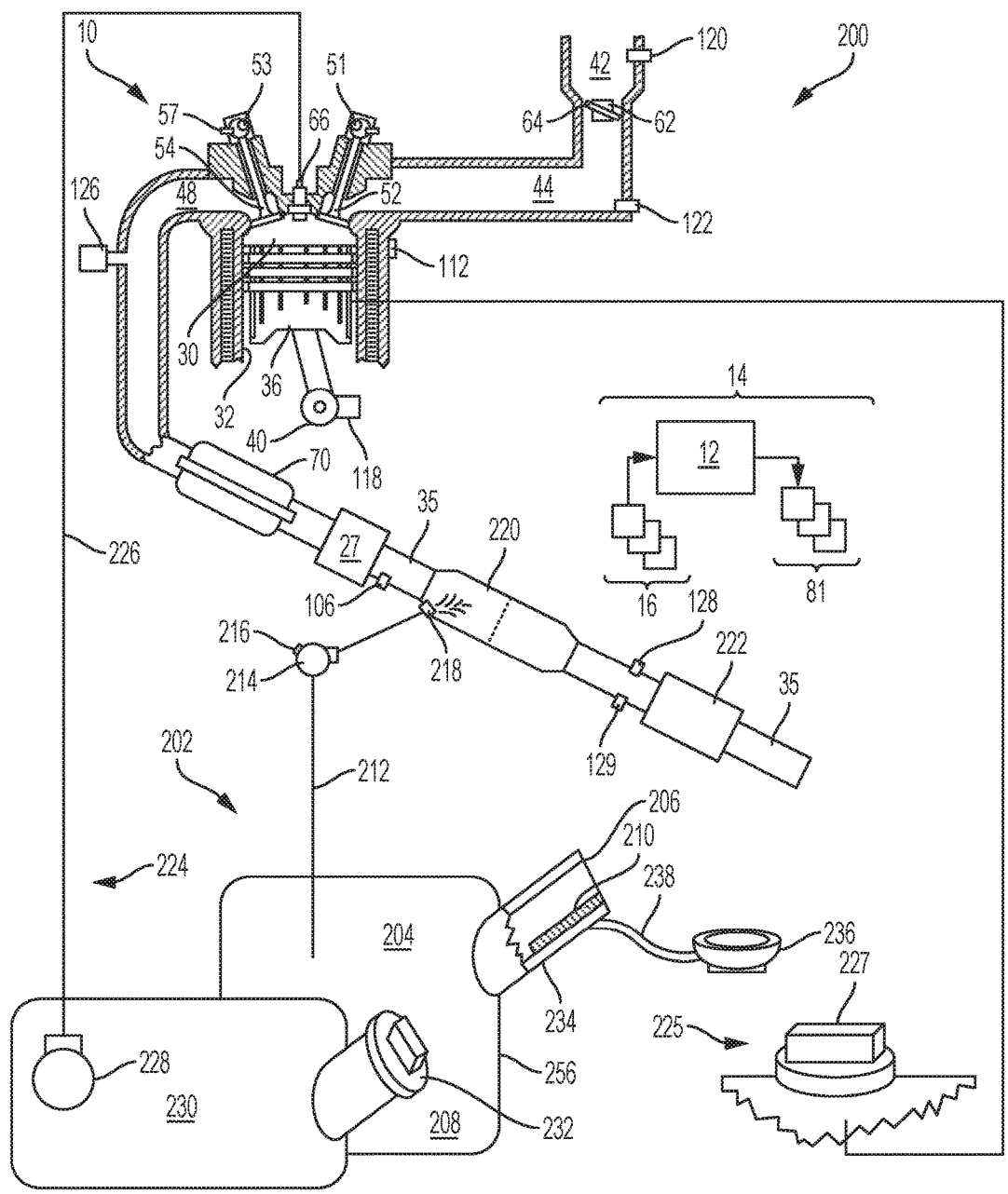
FIG. 1 is a schematic diagram showing one cylinder of a multi-cylinder diesel engine in accordance with the present disclosure.

FIG. 1 is a schematic diagram showing one cylinder of multi-cylinder engine 10, which may be included in a propulsion system of an automobile. Engine 10 may be controlled at least partially by a control system including controller 12 and by input from a vehicle operator 132 via an input device 130. In this example, input device 130 includes an accelerator pedal and a pedal position sensor 134 for generating a proportional pedal position signal PP. Combustion chamber (i.e., cylinder) 30 of engine 10 may include combustion chamber walls 32 with piston 36 positioned therein. Piston 36 may be coupled to crankshaft 40 so that reciprocating motion of the piston is translated into rotational motion of the crankshaft. Crankshaft 40 may be coupled to at least one drive wheel of a vehicle via an intermediate transmission system. Further, a starter motor may be coupled to crankshaft 40 via a flywheel to enable a starting operation of engine 10. A lubrication system in the form of oil distribution system 136 may be provided to direct oil to lubricate the engine 10. Combustion chamber 30 may receive intake air from intake manifold 44 via intake passage 42 and may exhaust combustion gases via exhaust passage 48. Intake manifold 44 and exhaust passage 48 can selectively communicate with combustion chamber 30 via respective intake valve 52 and exhaust valve 54. In some embodiments, combustion chamber 30 may include two or more intake valves and/or two or more exhaust valves.

In this example, intake valve 52 and exhaust valves 54 may be controlled by cam actuation via respective cam actuation systems 51 and 53. Cam actuation systems 51 and 53 may each include fixed cam timing, or may include one or more cams and may utilize one or more of cam profile switching (CPS), variable cam timing (VCT), variable valve timing (VVT) and/or variable valve lift (VVL) systems that may be operated by controller 12 to vary valve operation. The position of intake valve 52 and exhaust valve 54 may be determined by position sensors 55 and 57, respectively. In alternative embodiments, intake valve 52 and/or exhaust valve 54 may be controlled by electric valve actuation. For example, cylinder 30 may alternatively include an intake valve controlled via electric valve actuation and an exhaust valve controlled via cam actuation including CPS and/or VCT systems.

Fuel injector 66 is shown coupled directly to combustion cylinder 30 for injecting fuel directly therein in proportion to the pulse width of signal FPW received from controller 12 via electronic driver 68. In this manner, fuel injector 66 provides what is known as direct injection of fuel into combustion cylinder 30. The fuel injector may be mounted on the side of the combustion cylinder or in the top of the combustion cylinder, for example. Fuel may be delivered to fuel injector 66 by a fuel delivery system 224 including a fuel tank 230, and a fuel pump 228 (discussed more later). In some embodiments, combustion cylinder 30 may alternatively or additionally include a fuel injector arranged in intake passage 42 in a configuration that provides what is known as port injection of fuel into the intake port upstream of combustion cylinder 30.

Intake passage 42 may include a charge motion control valve (CMCV) and a CMCV plate (not shown) and may also include a throttle 62 having a throttle plate 64. In this particular example, the position of throttle plate 64 may be varied by controller 12 via a signal provided to an electric motor or actuator included with throttle 62, a configuration that may be referred to as electronic throttle control (ETC). In this manner, throttle 62 may be operated to vary the intake air provided to combustion cylinder 30 among other engine combustion cylinders. Intake passage 42 may include a mass air flow sensor 120 and a manifold air pressure sensor 122 for providing respective signals MAF and MAP to controller 12.

Intake manifold 44 may include a throttle 62 having a throttle plate 64. However, in other examples, the throttle may be located in intake passage 42. In this particular example, the position of throttle plate 64 may be varied by controller 12 via a signal provided to an electric motor or actuator included with throttle 62, a configuration that is commonly referred to as electronic throttle control (ETC). In this manner, throttle 62 may be operated to vary the intake air and/or EGR provided to combustion chamber 30 among other engine cylinders. The position of throttle plate 64 may be provided to controller 12 by throttle position signal TP. Intake passage 42 may include a mass air flow sensor 120 and a manifold air pressure sensor 122 for providing respective signals MAF and MAP to controller 12.

In this embodiment the engine is a diesel engine configured to combust diesel fuel (e.g. petroleum diesel or biodiesel) via compression ignition. Exhaust gas sensor 126 is shown coupled to exhaust passage 48 upstream of emission control device 70. Sensor 126 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), a NO.sub.x, HC, or CO sensor. Universal Exhaust Gas Oxygen (UEGO) sensor 126 is shown coupled to exhaust manifold 48 upstream of catalytic converter 70. Alternatively, a two-state exhaust gas oxygen sensor may be substituted for UEGO sensor 126.

Emission control device 70 is shown arranged along exhaust passage 48 downstream of exhaust gas sensor 126. Device 70 may include a diesel oxidation catalyst (DOC) and a selective catalytic reduction (SCR) catalyst. At least one diesel particulate filter (DPF) 27 may be coupled downstream of the emission control device 70. The DPF may be manufactured from a variety of materials including cordierite, silicon carbide, and other high temperature oxide ceramics. Once soot accumulation has reached a predetermined level (identified via pressure drop, for example), regeneration of the filter may be initiated. Filter regeneration may be accomplished by heating the filter to a temperature that will burn soot particles at a faster rate than the deposition of new soot particles, for example, 400-600.degree. C. In one example, the DPF can be a catalyzed particulate filter containing a washcoat of precious metal, such as platinum, to lower soot combustion temperature and also to oxidize hydrocarbons and carbon monoxide to carbon dioxide and water.

The engine 10 may include a control system 14. Control system 14 is shown receiving information from a plurality of sensors 16 and sending control signals to a plurality of actuators 81. As one example, sensors 16 may include exhaust flow rate sensor 126 configured to measure a flow rate of exhaust gas through the exhaust passage 35, exhaust gas sensor (located in exhaust manifold 48), temperature sensor 128, pressure sensor 129 (located downstream of emission control device 70), and PM sensor 106. Other sensors such as additional pressure, temperature, air/fuel ratio, exhaust flow rate and composition sensors may be coupled to various locations in the vehicle system 6. As another example, the actuators may include fuel injectors 66, throttle 62, DPF valves that control filter regeneration (not shown), a motor actuator controlling PM sensor opening (e.g., controller opening of a valve or plate in an inlet of the PM sensor), etc. As yet another example, the actuators may include switches coupled to PM measurement circuitry. The control system 14 may include a controller 12. The controller 12 may be configured with computer readable instructions stored on non-transitory memory. The controller 12 may receive signals from the various sensors, may process the signals, and may employ various actuators of to adjust engine operation based on the received signals and instructions stored on a memory of the controller 12.

As described above, FIG. 1 shows only one cylinder of a multi-cylinder engine, however it can be appreciated that each cylinder may similarly include its own set of intake/exhaust valves, fuel injector, etc.

Embodiments in accordance with the present disclosure may provide a system 200 for use with a diesel exhaust fluid system 202. The system 200 may include a container 204 having an opening 206 to receive a diesel exhaust fluid 208. A reactive device 210 may be located near the opening 206, and may be reactive upon exposure to one or more predetermined components potentially present in a fluid pourable into the container 204 through the opening 206, and not reactive to the diesel exhaust fluid. The container 204 may be a DEF storage tank.

The one or more predetermined components may be determined empirically, and/or selected from a list and/or from a database, and the like. A selection criteria may be used wherein the one or more predetermined components may be chosen for not being included in another preselected list, for example, for not being included in a list of acceptable ingredients, or concentrations permitted to be present in the DEF storage tank. Other methods of selection may be used. The reactive device 210 may be a hydrocarbon sensitive material.

The system 200 may be included in the engine 10. Other embodiments may be included in other mechanisms, for example a DEF refilling system. The system 200 illustrated may also include a conduit 212 and a pump 214 that may be actuated with switch 216 which may be controlled by the controller 12. Upon actuation the pump 214 may inject, or spray, a metered amount of DEF into the exhaust stream 35 with an injector 218. The diesel exhaust fluid (DEF) may have a concentration of 32.5% urea and 67.5% de-ionized water, or an appropriate different concentration. Upon mixing with the exhaust 35 the urea may decompose into ammonia and carbon dioxide. The exhaust may move through a SCR catalyst 220 where the NOx included in the exhaust may be chemically reduced by the ammonia ($NH_3$) into water ($H_2O$) and nitrogen ($N_2$), and released through the exhaust 35. The exhaust may also pass through a muffler 222.

The system 200 may also include a fuel system 224 including a fuel line 226 to provide diesel fuel to the fuel injector 66. A fuel rail (not shown) may be included. A fuel pump 228 may pump the fuel from a fuel tank 230. During a refueling operation a diesel fuel cap 232 may be removed, providing access into the tank 230. The engine 10 may also include an oil system 225 including an oil cap 227 to provide access for adding oil. The fuel cap 232, the oil cap 227 and other caps, or access points, which may provide access to various liquids which may be located fairly close to the DEF cap 236 in, for example, an engine compartment.

Figure 2:
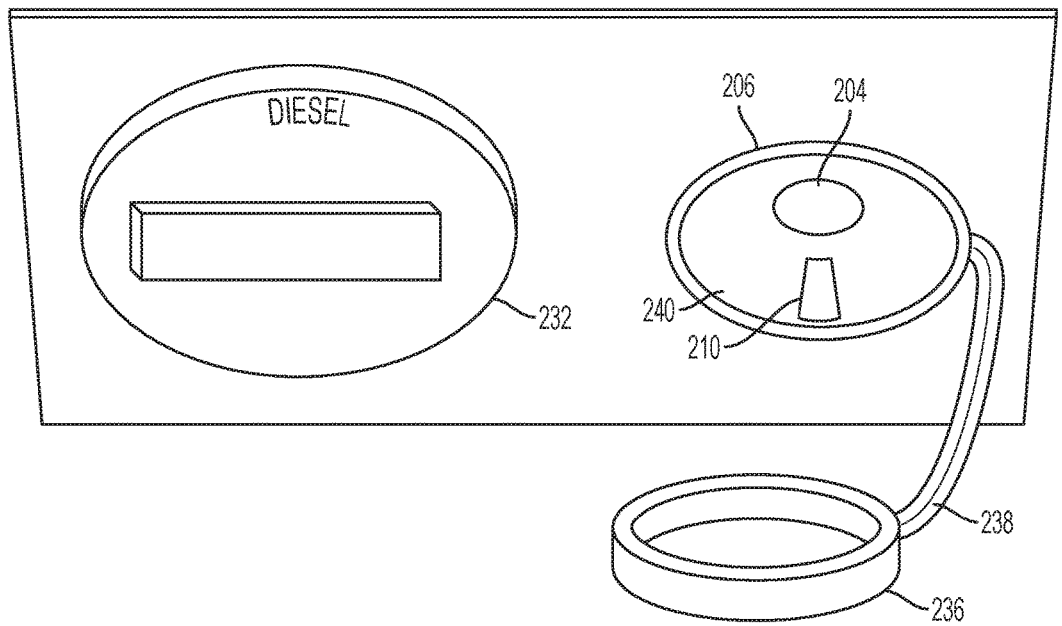
FIG. 2 is a partial representation of a view showing a diesel fuel cap in close proximity to a DEF refill port, and a contamination indicator in accordance with the present disclosure.

FIG. 2 is a partial representation of a view toward a part of an engine 10 showing a diesel fuel cap 232 and an opening 206 to a diesel exhaust fluid (DEF) storage tank 204 in close proximity to each other. The figure also illustrates an inside of the container neck 234 with the reactive device 210 visible at an entry region 240 of the neck 234. The inside of the neck 234 is made visible since the DEF cap 236 has been removed. The cap 236 may be held from loss via a tether 238.

The reactive device 210 may be configured to change appearance upon being exposed to the one or more predetermined components. As mentioned the reactive device 210 may be a hydrocarbon sensitive material. The hydrocarbon sensitive material may include a dye comprising a chemical known to change color upon being exposed to a hydrocarbon. The reactive device 210 may react by changing color.

Figure 3:
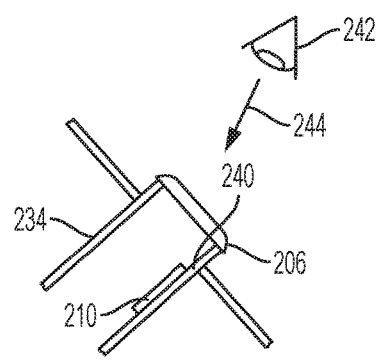
FIG. 3 is a partial sectional view showing the neck of a DEF storage tank and an observer observing an indicator in accordance with the present disclosure.

FIG. 3 is a partial sectional view showing the neck 234 of the storage tank 204 and how an observer 242 may look past the opening 206, and view, as shown with view arrow 244, the entry region 240 at an inside of the neck 234. The reactive device 210 may also be visible which may enable the observer 242 to see whether or not the reactive device 210 has reacted to exposure to the one or more predetermined components present in a fluid that may have been poured, or splashed, or the like, into the DEF storage container 204 which may have contaminated the DEF.

Turning now to FIGS. 4A-6B wherein various additional example embodiments are illustrated showing a reactive device 210, or DEF indicator 210, in example first states 246 in FIGS. 4A, 5A and 6A, and example second states 248 in FIGS. 4B, 5B and 6B. FIGS. 4A-6B illustrate examples wherein in addition to, or as an alternative to, changing color the reactive device may react by changing one or more of shape and configuration upon being exposed to the one or more elements considered as contaminants. For example, and as discussed, the reactive device 210, or DEF indicator 210 device may be reactive to selected chemical components not included the diesel exhaust fluid.

FIGS. 4A-4B illustrate an example wherein an adhesive 250 may be dissolved, or weakened, by a contaminant to effect a change in the indicator 210 from a compressed discoid shape to a distended discoid shape. Other embodiments may use an adhesive, and may show reaction by simply falling off upon dissolution of the adhesive 250. Other embodiments may provide an indicator 210 that may dissolve substantially completely.

FIGS. 5A-5B and 6A-6B illustrate respective examples wherein, upon dissolution of an adhesive 250 by a contaminant, the reactive device 210 may react by changing shape, or configuration, in a way to interfere with one or both of: inserting a nozzle of a DEF refill source, and replacing a DEF cap 236. In the first case (5A-5B), a portion of the reactive device 210 may extend at least partway across the opening 206, in the second case (6A-6B), the reactive device 210 may extend through the opening 206, for example extend from the neck 234 of the container 204, making replacing the cap 236 difficult, or impossible. Either case may provide an indication of contamination.

In some embodiments, the DEF container 204, or DEF storage tank 204, may be disposed within a diesel exhaust fluid delivery and/or refill mechanism including one of: a stationary refill tank adjacent to which a diesel powered engine that may be driven to receive a refill quantity of diesel exhaust fluid; and a movable refill tank disposed on a refilling vehicle. The reactive device 210, being exposed may be considered to include being contacted or impacted by fluid passing through the opening, wherein being impacted may include one or more of: being splashed; having the fluid poured thereon; and having the fluid run over and/or through the reactive device 210. The reactive device may be positioned in close enough proximity to be impacted by fluid passing through the opening. The fluid may, for example, be accidentally poured, or splashed into the container in a DEF refill operation.

Embodiments may provide a diesel exhaust fluid contamination indicator 210 that may include an indicator body 252. An attachment mechanism 254 may be included to attach the body 252 to an inside surface 240 of a conduit 234 leading into a majority portion 256 (FIG. 1) of a diesel exhaust fluid container 204. At least a portion of the body 252 may be reactive to change from a first state 246 to a second state 248 upon being contacted by a predetermined concentration of a liquid from a predetermined set of components.

As discussed, in some examples, the first state 246 may be a first color, and the second state 248 may be a second color. In other examples the first state 246 may be a first shape, and the second state 248 may be a second shape. In still other examples the first state 246 may be a first configuration, and the second state 248 may be a second configuration.

The body 252 may include a first part 256, a second part 258, and a junction 260 connecting the first part 256 to the second part 258. The junction 260 may be distortable and able to store energy for a reactive force upon being distorted. The body 254 may be, or may include, for example, a spring like material such as a metal, or an elastomer.

A portion of each of the first part 256 and the second part 258 distal from the junction 260 may be configured to be joined together with an adhesive 250. The joining of the distal portions 262, 264 may cause the distortion of the junction 260 and a change in shape and/or configuration of the body 254 from a second state 248 to a first state 246. The adhesive 250 may be dissolvable and/or weakened upon exposure to the liquid containing the contamination, thereby disjoining the distal portions 262, 264 and allowing the reactive force to substantially return the body to the second state 248.

In the embodiment illustrated in FIGS. 4A-4B the diesel exhaust fluid contamination indicator 210 may include a body 254 that may define a hollow substantially discoid shape. The first part 256 may be a bottom of the discoid shape, and the second part 258 may be a top of the discoid shape. The attachment mechanism 254 may attach an outside surface of the bottom to the inside surface of a conduit 234, i.e. the neck 234. The adhesive 250 may attach an inside surface of the top to an inside surface of the bottom to achieve the first state 246 and form the body 252 to have a relatively depressed middle portion. Upon dissolving and/or sufficiently weakening the adhesive 250, the reactive force may be allowed to move the top away from the bottom to achieve the second state 248 and to form the body 252 to have a relatively less depressed or protruding top.

In this way, a change in appearance of the body 252 from a discoid, or button type, shape with a relatively depressed top middle surface, to a discoid shape with a less depressed, or protruding top middle surface will provide to, for example a technician and/or owner of the vehicle, a visual indication of contamination of the DEF. Also, or instead, in this way, the indicator 210 may provide a tactile indication in that a person may press on the top middle and feel that the hollow discoid shape may be suppressed against the force of the junction, and conclude the adhesive has been dissolved, and has "let go" of the top of the body. The change in shape of the body may also be determined by a sensor to provide a signal to, for example, the controller 12, or to an intermediate system, or to a diagnostic device, and the like. The determination that the indicator 210 is in the second 248 (or contaminated) state may prompt one or more automated, or semi-automated, operations to be performed. Such operations may include, for example, a notification, a warning, mitigation measures, and the like.

In the embodiments illustrated in FIGS. 5A-5B, and FIGS. 6A-6B the diesel exhaust fluid contamination indicator 210 may include a first part 256 and the second part 258 which may be elongate members coupled together by a distortable junction 260. The first state 246 being the first part 256 folded onto the second part 258 thereby bending the junction 260 to store energy for the reactive force. The first and second parts 256, 258 may be joined at respective distal ends 262, 264 with the adhesive 250. The body 252 may be disposed in the second state 248 upon the dissolving and/or sufficiently weakening of the adhesive 250 allowing the reactive force to at least partly unbend the junction 260 and to change the relative orientation of the first part 256 and second part 258. In this way, the indicator 210 may change appearance which may trigger various actions such as discussed herein. Also in this way, the indicator 210 may change shape or configuration such that the first or the second part may interfere with an action that may otherwise be taken by the owner, or technician, or the like. For example, when in the second state 248 the indicator may interfere with replacing a cap 236 onto the opening 206 of the DEF, or interfere with inserting a nozzle into the neck 234 of the DEF storage tank 204.

The embodiment shown in FIGS. 5A-5B shows the indicator 210 oriented substantially transverse to a central axis 266 of the neck 234. The embodiments shown in FIGS. 5A-5B show the indicator 210 oriented substantially parallel with the central axis 266.F FIG. 5B illustrates the case wherein the reactive device in its second configuration may position a movable portion, in this case the second part 258 to extend at least partway across the opening, i.e. to extend at least partway across the entry region, thereby at least partly obstructing, for example, a refill nozzle to be inserted into the opening. In this way, the indicator 210 may serve to provide a visual and/or, a tactile, and/or a practical, indication and/or notification that the DEF has been contaminated.

FIGS. 6A-6B illustrates the case wherein the wherein the body of the indicator 210 is oriented substantially parallel with a central axis of an entry region of the DEF storage tank. FIG. 6B illustrates the indicator 210 in its second configuration which may position a movable portion, in this case the second part 258 to extends out through an opening of the neck 234. In this way, the second part may serve as an obstruction to reattaching the cap 236 of the DEF storage tank 204. This may a serve as a substantially immediate notification to the individual who introduced the contaminant that the DEF has been contaminated. In this way, the DEF indicator may also serve as a warning mechanism that something is wrong and the engine should not be started and/or that a trained engine technician should be consulted. One embodiment may couple proper cap 236 replacement with engine 10 restart which may involve the engine controller 12.

Various embodiments may provide a method of equipping a diesel exhaust fluid (DEF) storage tank to be contamination evident. The method may include placing a contaminant reactive indicator in a first state in an entry region of the DEF storage tank. The method may also include allowing a first user or operator to pour a liquid into the DEF storage tank. Then possibly, but not necessarily, at a relatively later time, allowing the first user or operator, or a second user or operator, to visually inspect the indicator. The indicator may be inspected by removing the cap 236 to the DEF storage tank 204 and looking into the neck of the container. This may be accomplished manually, or in an automated, or semi-automated fashion. The operator may be a machine, or robot, or the like. A human inspector may use a light source, and/or a metering device, or camera, or the like. Upon inspection the operator may conclude, either: no contamination has occurred to the liquid in the DEF storage tank if the indicator is in the first state, or contamination has occurred to the liquid in the DEF storage tank if the indicator is, instead, in a second state.

The conclusion, or results of the conclusion, may be effected by one or more mechanized actions that may be determined, and or controlled, by a computer controlled algorithm, and or one or more sensors. In some cases a handheld, or otherwise positioned, light meter, or image recognition device, with at light source may automatically, or semi-automatically, determine the state of the indicator.

Various other embodiments may provide a method of determining a purity condition of a diesel exhaust fluid (DEF) in a DEF storage tank. The method may include removing a storage tank cap from a neck of the storage tank, and then visually inspecting a hydrocarbon reactive indicator located at an entry region at an inside of the neck. The method may also include determining if the indicator is in a first state or in a second state, the second state indicative of exposure to a hydrocarbon. In some cases, the removing and visually inspecting is included in a repairing and/or maintaining operation of a diesel engine. The repairing and/or maintaining operation may be automated or semi-automated; and may or may not effect one or more mechanized actions that may be determined, and or controlled by a computer controlled algorithm.

It will be appreciated by those skilled in the art that although the present disclosure has been described by way of example with reference to one or more embodiments it is not limited to the disclosed embodiments and that one or modifications to the disclosed embodiments or alternative embodiments could be constructed without departing from the scope of the present disclosure.

Accordingly, it will be appreciated that the configurations and methods disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A system for use with a diesel exhaust fluid comprising:
a diesel exhaust fluid container having an opening; and
a reactive device contacting received diesel exhaust fluid, the reactive device changing to a second state upon exposure to one or more liquid components, the reactive device remaining in a first, not reacted state upon exposure to diesel exhaust fluid containing urea and water.

2. The system of claim 1, wherein the reactive device changes to the second state upon contact with hydrocarbons.

3. The system of claim 2, wherein the reactive device includes a dye that changes color upon contact with the hydrocarbons.

4. The system of claim 1, wherein the reactive device is configured to change states of appearance upon being contacted by the one or more liquid components.

5. The system of claim 1, wherein the reactive device reacts by changing states of color.

6. The system of claim 1, wherein the reactive device reacts by changing states of one or more of color, shape, and configuration upon being exposed to the one or more liquid components.

7. The system of claim 1, wherein the reactive device changes to the second state by changing shape and creating contact between the reactive device and one or both of a cap, and a nozzle of a refill source when inserted into the opening.

8. The system of claim 1, wherein the diesel exhaust fluid has a concentration of 32.5% urea and 67.5% de-ionized water, and the reactive device changes states upon exposure to chemical components not included in the diesel exhaust fluid.

9. The system of claim 1, wherein the diesel exhaust fluid container is disposed within a diesel engine system.

10. The system of claim 1, further including one of: a stationary refill tank adjacent to which a diesel powered engine can be driven to receive a refill quantity of diesel exhaust fluid, and a movable refill tank disposed on a refilling vehicle.

11. The system of claim 1, wherein being exposed includes being impacted by fluid passing through the opening, and wherein being impacted includes one or more of being splashed, having a fluid poured thereon, and having the fluid run over or through.

12. A diesel exhaust fluid contamination indicator comprising:
an indicator body;
the indicator body attached to an inside surface of a conduit leading into a container;
a portion of the indicator body changing from a first state of appearance to a second state of appearance upon being contacted by a concentration of a liquid from a set of components and one of the set being hydrocarbon fuel, the indicator body remaining in the first state upon contact with diesel exhaust fluid containing urea.

13. The diesel exhaust fluid contamination indicator of claim 12, wherein the first state of appearance is a first color, and the second state of appearance is a second color.

14. The diesel exhaust fluid contamination indicator of claim 12, wherein the first state of appearance is a first shape, and the second state of appearance is a second shape.

15. The diesel exhaust fluid contamination indicator of claim 12, wherein:

the indicator body includes a first part, a second part, and a junction connecting the first part to the second part, the junction being distortable and able to store energy for a reactive force upon being distorted;

a portion of each of the first part and the second part distal from the junction configured to be joined together with an adhesive, the joining of the distal portions causing the distortion of the junction and a change in shape of the indicator body from the second state of appearance to the first state of appearance; and the adhesive being weakened upon exposure to the liquid containing a contaminant, thereby disjoining the distal portions and allowing the reactive force to substantially return the indicator body to the second state of appearance.

16. The diesel exhaust fluid contamination indicator of claim 15, wherein:

the indicator body defines a hollow substantially discoid shape, the first part is a top of the discoid shape, and the second part is a bottom of the discoid shape;

an outside surface of the bottom attached to the inside surface of the conduit; and the adhesive attaching an inside surface of the top to an inside surface of the bottom to achieve the first state of appearance and form the indicator body to have a depressed middle portion, and upon weakening the adhesive the top moves away from the bottom to achieve the second state of appearance and to form the body to have a less depressed top.

17. The diesel exhaust fluid contamination indicator of claim 15, wherein:

the first part and the second part are elongate members coupled together by the distortable junction, the first state of appearance being the first part folded onto the second part thereby bending the junction to store energy for the reactive force, and, when in the first state of appearance, the first and second parts are joined at respective distal ends with the adhesive; and the indicator body is disposed in the second state of appearance upon the weakening of the adhesive the junction distorting and changing a relative orientation of the first and second parts.

18. The diesel exhaust fluid contamination indicator of claim 17, wherein the indicator body is oriented substantially transverse to a central axis of an entry region of a diesel exhaust fluid storage tank, and, when in the second state of appearance, the second part extends across the entry region.

19. The diesel exhaust fluid contamination indicator of claim 17, wherein the indicator body is oriented substantially parallel with a central axis of an entry region of a diesel exhaust fluid storage tank, and, when in the second state of appearance, the second part extends out through an opening of the conduit.

20. A method of equipping a diesel exhaust fluid (DEF) storage tank to be contamination evident, comprising:

receiving liquid DEF past a contaminant reactive indicator in a first state in an entry region of the DEF storage tank, the liquid DEF received into the DEF storage tank, the entry region of the DEF storage tank adjacent an entry region of a diesel fuel tank;

generating a visual indication at the contaminant reactive indicator of:

no contamination upon receiving the liquid DEF by retaining the first state, wherein the liquid DEF includes urea and water; and receiving liquid diesel fuel past the contaminant reactive indicator in the first state; and generating a visual indication at the contaminant reactive indicator that contamination has occurred by a transition from the first state to a second state upon liquid diesel fuel contacting the contaminant reactive indicator.

* * * * *